United States Patent [19]

Skuballa et al.

[11] Patent Number: 5,157,042
[45] Date of Patent: Oct. 20, 1992

[54] 3-OXA-5-FLUORO-CARBACYCLINS, THEIR PREPARATION AND USE AS MEDICINAL AGENTS

[75] Inventors: Werner Skuballa; Bernd Raduechel; Helmut Vorbrueggen, all of Berlin; Jorge Casals-Stenzel, Mainz; Gerda Mannesmann, Cologne; Michael H. Town, Berlin, all of Fed. Rep. of Germany

[73] Assignee: Schering Aktiengesellschaft, Berlin and Bergkamen, Fed. Rep. of Germany

[21] Appl. No.: 713,002

[22] Filed: Jun. 10, 1991

Related U.S. Application Data

[63] Continuation of Ser. No. 508,508, Apr. 12, 1990, abandoned, which is a continuation of Ser. No. 351,744, May 15, 1989, abandoned, which is a continuation of Ser. No. 115,747, Nov. 2, 1987, abandoned, which is a continuation of Ser. No. 931,115, Nov. 17, 1986, abandoned, which is a continuation of Ser. No. 763,697, Aug. 8, 1985, abandoned, which is a continuation of Ser. No. 510,129, Jul. 1, 1983, abandoned.

[30] Foreign Application Priority Data

Jul. 2, 1982 [DE] Fed. Rep. of Germany ....... 3225288

[51] Int. Cl.⁵ .................. C07C 177/00; A61K 31/557
[52] U.S. Cl. .................. 514/530; 514/573; 514/623; 560/119; 562/501; 564/188
[58] Field of Search .......... 560/119; 562/501; 564/188; 514/530, 573, 623

[56] References Cited

U.S. PATENT DOCUMENTS 4,306,075 12/1981 Aristaff .................. 560/56
4,423,067 12/1983 Skuballa .................. 560/119
4,618,626 10/1988 Skuballa .................. 514/503

FOREIGN PATENT DOCUMENTS 0056208 12/1980 European Pat. Off.
2070596 9/1981 United Kingdom.

Primary Examiner—Robert Gerstl
Attorney, Agent, or Firm—Millen, White & Zelano

[57] ABSTRACT

Carbacyclin derivatives of Formula I

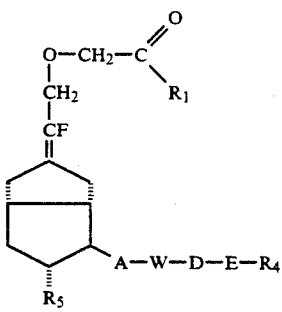

wherein
$R_1$ is $OR_2$, wherein $R_2$ is hydrogen, alkyl, cycloalkyl, aryl,

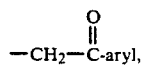

or a heterocyclic residue; or $R_1$ is $NHR_3$ wherein $R_3$ is an acid residue (acyl) or $R_2$;
A is $-CH_2-CH_2-$, trans$-CH=CH-$, or $-C\equiv C-$;
W is a free or functionally modified hydroxymethylene group or a free or functionally modified

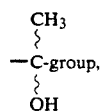

wherein the OH-group can be in the $\alpha$- or $\beta$-position;
D is

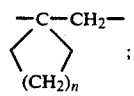

a straight-chain, saturated aliphatic group of 1–10 carbon atoms; or a branched, saturated or straight-chain or branched, unsaturated aliphatic group of 2–10 carbon atoms; all of which are substituted by fluorine atoms;
n is 1, 2, or 3;
E is a direct bond, $-C\equiv C-$, or $-CR_6=CR_7-$, wherein $R_6$ is hydrogen or alkyl of 1–5 carbon atoms and $R_7$ is hydrogen, halogen or alkyl of 1–5 carbon atoms;
$R_4$ is an aliphatic group, cycloalkyl, optionally substituted aryl, or a heterocyclic group; and
$R_5$ is a free or functionally modified hydroxy group; and
when $R_1$ is OH, the salts thereof with physiologically compatible bases,
are valuable pharmacological agents.

13 Claims, No Drawings

3-OXA-5-FLUORO-CARBACYCLINS, THEIR PREPARATION AND USE AS MEDICINAL AGENTS

This application is a continuation of Ser. No. 07/508,508, filed Apr. 12, 1990, which is a continuation of Ser. No. 07/351,744, filed May 15, 1989, which is a continuation of Ser. No. 07/115,747, filed Nov. 2, 1987, which is a continuation of Ser. No. 06/931,115, filed Nov. 17, 1986, which is a continuation of Ser. No. 06/763,697, filed Aug. 8, 1985, which is a continuation of Ser. No. 06/510,129, filed Jul. 1, 1983, and now abandoned.

BACKGROUND OF THE INVENTION

The present invention relates to novel prostacyclin derivatives, a process for their preparation, and to their use as medicinal agents.

(5E)- and (5Z)-6a-carbaprostaglandin $I_2$ analogs are disclosed in German Unexamined Laid-Open Applications DOS's 2,845,770; 2,900,352 (U.S. Pat. No. 4,322,435); 2,902,442 (U.S. Pat. No. 4,307,112); 2,904,655 (U.S. Pat. No. 4,238,414); 2,909,088; 3,048,906; and 2,912,409. The nomenclature of the compounds of this invention is based on a proposal by Morton and Brokaw (J. Org. Chem. 44 : 2880 [1979]). The synthesis of these compounds yields in all cases two double-bond isomers characterized by the symbols (5E) or (5Z). The two isomers of this prototype are clarified by the following structural formulae:

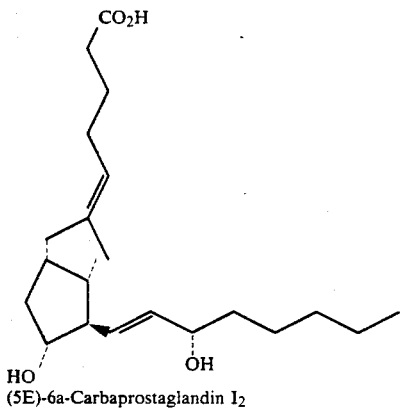
(5E)-6a-Carbaprostaglandin $I_2$

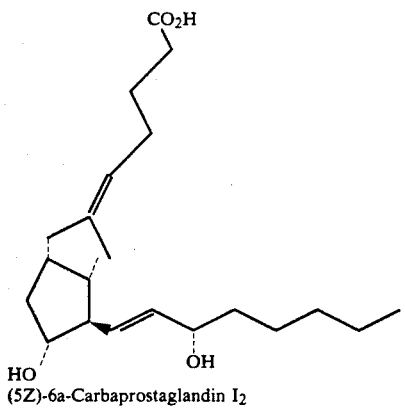
(5Z)-6a-Carbaprostaglandin $I_2$

It is known from the very voluminous state of the art of prostacyclins and their analogs that this class of compounds is suited, due to its biological and pharmacological properties, for the treatment of mammals, including man. The use of these compounds as medicinal agents, however, frequently meets with difficulties since their period of effectiveness is too short for therapeutic purposes. All structural modifications attempt to increase the duration of effectiveness as well as the selectivity of efficacy

SUMMARY OF THE INVENTION

Accordingly, it is an object of this invention to provide new carbacyclins having such improved properties.

Upon further study of the specification and appended claims, further objects and advantages of this invention will become apparent to those skilled in the art.

These objects have been achieved by providing new carbacyclin derivatives of Formula I

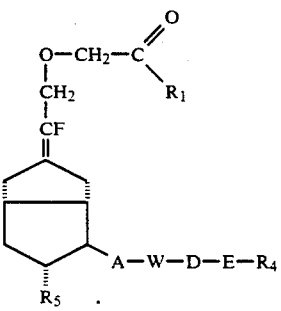

wherein $R_1$ is $OR_2$, wherein $R_2$ is hydrogen, alkyl, cycloalkyl, aryl,

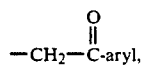

or a heterocyclic residue; or $R_1$ is $NHR_3$ wherein $R_3$ is an acid residue (acyl) or $R_2$;

A is $-CH_2-CH_2-$, $trans-CH=CH-$, or $-C\equiv C-$;

W is a free or functionally modified hydroxymethylene group or a free or functionally modified

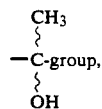

wherein the OH-group can be in the α- or β-position;

D is

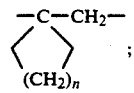

a straight-chain, saturated aliphatic group of 1-10 carbon atoms; or a branched, saturated or straight-chain or branched, unsaturated aliphatic group of 2-10 carbon atoms; all of which are optionally substituted by fluorine atoms;

n is 1, 2, or 3;

E is a direct bond, —C≡C—, or —CR$_6$=CR$_7$— wherein R$_6$ is hydrogen or alkyl of 1–5 carbon atoms, and R$_7$ is hydrogen, halogen or alkyl of 1–5 carbon atoms, R$_4$ is an aliphatic group, cycloalkyl, optionally substituted aryl, or a heterocyclic group; and R$_5$ is a free or functionally modified hydroxy group; and when R$_1$ is OH, the salts thereof with physiologically compatible bases.

It has now been found that longer duration of effectiveness, higher selectivity, and improved efficacy can be obtained in carbacyclins by substitution of the methylene group in the 3-position by oxygen and of the hydrogen atom in the 5-position by fluorine. The compounds of this invention have blood-pressure-lowering and bronchodilatory effects. They are furthermore suitable for vasodilation, inhibition of thrombocyte aggregation and of gastric acid secretion.

DETAILED DISCUSSION

The compounds of Formula I include (5E)- as well as (5Z)-isomers.

Suitable alkyl groups R$_2$ include straight-or branched-chain alkyl groups of 1–10 carbon atoms, e.g., methyl, ethyl, propyl, isopropyl, butyl, isobutyl, tert-butyl, pentyl, isopentyl, neopentyl, heptyl, hexyl, decyl. The alkyl groups R$_2$ can optionally be mono- to poly-substituted (e.g., 2–5 substituents) by halogen atoms, hydroxy groups, C$_1$–C$_4$-alkoxy groups, optionally substituted C$_6$–C$_{10}$-aryl groups, di-C$_1$–C$_4$-alkylamines, and tri-C$_1$–C$_4$-alkylammonium. Suitable substituted aryl groups include those described below for R$_2$ per se. Monosubstituted alkyl groups are preferred. Examples of substituents include fluorine, chlorine, bromine, phenyl, dimethylamino, diethylamino, methoxy, ethoxy, etc. Preferred alkyl groups R$_2$ are those of 1–4 carbon atoms in the alkyl portion, e.g., methyl, ethyl, propyl, dimethylaminopropyl, isobutyl, butyl, etc.

Suitable aryl groups R$_2$ include substituted as well as unsubstituted aryl groups, for example phenyl, 1-naphthyl, and 2-naphthyl, each of which can be substituted by 1–3 halogen atoms, phenyl, 1–3 alkyl groups each of 1–4 carbon atoms, or a chloromethyl, fluoromethyl, trifluoromethyl, carboxy, hydroxy, or alkoxy group of 1–4 carbon atoms. Preferred is substituion in the 3- and 4-positions on the phenyl ring, for example by fluorine, chlorine, alkoxy, or trifluoromethyl, or in the 4-position by hydroxy.

Suitable cycloalkyl groups R$_2$ contain 3–10, preferably 5 or 6 carbon atoms in the ring. The rings can be substituted by alkyl groups of 1–4 carbon atoms. Examples include cyclopentyl, cyclohexyl, methylcyclohexyl, and adamantyl.

Suitable heterocyclic groups R$_2$ include 5- and 6-membered heterocycles containing at least one hetero atom, preferably nitrogen, oxygen, or sulfur, usually one such atom. The rings are normally aromatic. Examples include 2-furyl, 3-furyl, 2-thienyl, 3-thienyl, 2-pyridyl, 3-pyridyl, 4-pyridyl and others.

The aryl group in the

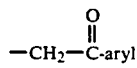

group for R$_2$ can be phenyl, α- or β-naphthyl, and each can be substituted by (a) 1–3 phenyl groups, which latter, in turn, can be substituted by 1–3 halogen atoms, such as F, Cl, or Br; or by (b) 1–3 C$_1$–C$_4$-alkoxy groups or by (c) 1–3 halogen atoms (F, Cl, Br). Single substitution by phenyl, C$_1$–C$_2$-alkoxy, chlorine, or bromine is preferred.

Suitable acid residues R$_3$, i.e., acyl groups, include physiologically compatible acid residues. Preferred acids are organic carboxylic acids and sulfonic acids of 1–15 carbon atoms pertaining to the aliphatic, cycloaliphatic, aromatic, aromatic-aliphatic, and heterocyclic series. These acids can be saturated, unsaturated and/or polybasic and/or substituted in the usual way. Examples of substituents are C$_1$–C$_4$-alkyl, hydroxy, C$_1$–C$_4$-alkoxy, oxo, or amino groups, or halogen atoms (F, Cl, Br). Thus, while the acids are often hydrocarbon in nature, many diverse equivalents exist and will be readily recognized by those of skill in the art.

The following carboxylic acids are recited as examples: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di-, and trichloroacetic acids, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy, or carboxy groups, nicotinic acid, isonicotinic acid, furan-2-carboxylic acid, cyclopentylpropionic acid, etc. Especially preferred acyl residues are those of up to 10 carbon atoms. Examples of suitable sulfonic acids include methanesulfonic acid, ethanesulfonic acid, isopropanesulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid, pyrrolidino-, piperidino-, piperazino-, N-methylpiperazino-, and morpholinosulfonic acids.

The hydroxy groups R$_5$ and those in W can be functionally modified, for example by etherification or esterification, wherein the free or modified hydroxy groups in W can be in the α- or β-position, free hydroxy groups being preferred.

The many suitable ether and acyl residues are well known to persons skilled in the art. Ether residues that can be easily split off are preferred, e.g., tetrahydropyranyl, tetrahydrofuranyl, α-ethoxyethyl, trimethylsilyl, dimethyl-tert-butylsilyl, and tribenzylsilyl. Suitable acyl residues include those mentioned for R$_3$. Thus, generally, these are C$_{1-15}$-hydrocarbon carboxylic and sulfonic acids and equivalents. Worth mentioning by name, for example, are acetyl, propionyl, butyryl, benzoyl, etc.

Suitable aliphatic groups R$_4$ include straight chained and branched, saturated (alkyl) and unsaturated (e.g., alkenyl) aliphatic residues, preferably alkyl groups, of 1–10, especially 1–7 carbon atoms which can optionally be substituted by optionally substituted aryl. Suitable substituents, on the latter aryl substituents, are those mentioned for the $R_2$ aryl groups per se. Examples include methyl, ethyl, propyl, butyl, isobutyl, tert-butyl, pentyl, hexyl, heptyl, octyl, butenyl, isobutenyl, propenyl, pentenyl, hexenyl, benzyl, and p-chlorobenzyl.

Cycloalkyl groups $R_4$ can contain 3-10, preferably 3-6 carbon atoms in the ring. The rings can also be substituted by alkyl groups of 1-4 carbon atoms. Examples include cyclopropyl, cyclobutyl, cyclopentyl, cyclohexyl, methylcyclohexyl, and adamantyl.

Examples of substituted and unsubstituted aryl groups $R_4$, include: phenyl, 1-naphthyl and 2-naphthyl, each of which can be substituted by 1-3 halogen atoms, phenyl, 1-3 alkyl groups of 1-4 carbon atoms each, or a chloromethyl, fluoromethyl, trifluoromethyl, carboxy, $C_1$-$C_4$-alkoxy, or hydroxy group. Substitution in the 3-and 4-positions on the phenyl ring is preferred, for example by fluorine, chlorine, $C_1$-$C_4$-alkoxy, or trifluoromethyl, or in the 4-position by hydroxy.

Suitable heterocyclic groups $R_4$ include 5- and 6-membered heterocycles containing at least one hetero atom, preferably nitrogen, oxygen, or sulfur, usually one such atom. The rings are usually aromatic. Examples include 2-furyl, 2-thienyl, 2-pyridyl, 3-pyridyl, 4-pyridyl, 3-furyl, 3-thienyl, etc.

The aliphatic groups D can be straight-chained or branched, saturated (alkylene) or unsaturated (alkenylene) residues, preferably saturated ones (alkylene) of 1-10, especially 1-5 carbon atoms which can optionally be substituted by fluorine atoms. Examples include: methylene, fluoromethylene, ethylene, 1,2-propylene, ethylethylene, trimethylene, tetramethylene, pentamethylene, 1-methyltetramethylene, 1-methyltrimethylene, etc., or also 1,1-trimethylene-ethylene

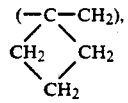

etc.

The alkyl groups $R_6$ and $R_7$ can be straight-chained or branched, alkyl groups of 1-4 carbon atoms, as mentioned above for $R_2$ and $R_4$. Suitable $R_7$ halogen atoms include chlorine and bromine, preferably chlorine.

The many conventional inorganic and organic bases suitable for salt formation with the free acids ($R_1$=OH), are known to those skilled in the art for the formation of physiologically compatible salts with prostaglandin-type compounds. Examples include: alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl)methylamine, etc.

This invention furthermore relates to a process for the preparation of carbacyclin derivatives of Formula I, comprising, conventionally etherifying, in the presence of a base, a compound of Formula II

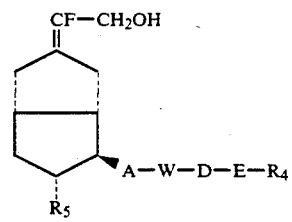

wherein $R_4$, $R_5$, A, W, D, and E are as defined above, optionally after blockage of any free hydroxy groups present, with a haloacetic acid derivative of Formula III

wherein
Hal is chlorine, bromine, or iodine, and
$R_8$ is alkyl or trialkylsilyl wherein the alkyl groups have 1-4 C-atoms, or an alkali metal (Na, Li, K), and
optionally, subsequently, in any desired sequence, separating isomers and/or liberating blocked hydroxy groups and/or esterifying or etherifying free hydroxy groups and/or esterifying a free carboxy group and/or saponifying an esterified carboxy group or converting a carboxy group into an amide or into a salt with a physiologically compatible base.

The reaction of the compound of Formula II with a haloacetic acid derivative of Formula III can be conducted at temperatures of 0° to 100° C., preferably 10°-80° C., in an aprotic solvent or solvent mixture, e.g., dimethyl sulfoxide, dimethylformamide, tetrahydrofuran, etc. The many suitable bases are well known to persons skilled in the art for etherification reactions, for example sodium hydride, potassium tert-butylate, butyllithium, etc.

The carbacyclin esters can be saponified according to methods known to those skilled in the art, such as, for example, using alkaline catalysts.

The introduction of the ester group —$OR_2$ as $R_1$, wherein $R_2$ is an alkyl group of 1-10 carbon atoms also takes place according to methods known to persons skilled in the art. The carboxy compounds can be reacted, for example, with diazohydrocarbons in a manner known per se. Esterification with diazohydrocarbons is effected, for example, by mixing a solution of the diazohydrocabon in an inert solvent, preferably in diethyl ether, with the carboxy compound in the same or a different inert solvent, e.g., methylene chloride, After the reaction is completed within 1-30 minutes, the solvent is removed and the ester purified as usual. Diazoalkanes are either known or can be produced by known methods [Org. Reactions 8 : 389-394 (1954)].

The introduction of the ester group —$OR_2$ as $R_1$ wherein $R_2$ is a substituted or unsubstituted aryl group also takes place by means of methods known to one skilled in the art. For example, the carboxy compounds and the corresponding arylhydroxy compounds can be reacted with dicyclohexylcarbodiimide in the presence of a suitable base, e.g., pyridine or triethylamine, in an inert solvent. The many suitable solvents include methylene chloride, ethylene chloride, chloroform, ethyl acetate, tetrahydrofuran, preferably chloroform. The reaction is conducted at temperatures of $-30°$ to $+50°$ C., preferably at $+10°$ C.

The ester group $-OR_2$ as $R_1$ wherein $R_2$ is

aryl can also h=introduced by conventionally reacting the carboxylate anion with the corresponding alkyl halogenide or ω-haloketone, especially for

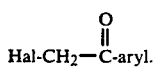

The definition of aryl is already give above.

The compounds containing OR2 groups wherein $R_2$ is cycloalkyl or a heterocyclic residue can be prepared by analogous methods, e.g., to those mentioned for $R_2$ alkyl and aryl groups.

The amide group $NHR_3$ can also be introduced as $R_1$ according to methods known to those skilled in the art. The carboxylic acids of Formula I ($R_2=H$) can first of all be converted into the corresponding mixed anhydride with the isobutyl ester of chloroformic acid, in the presence of a tertiary amine, e.g., triethylamine. The mixed anhydride is reacted with the alkali metal salt of the corresponding amide or with ammonia ($R_3=H$) in an inert solvent or solvent mixture, e.g., tetrahydrofuran, dimethoxyethane, dimethylformamide, hexamethylphosphoric triamide, at temperatures of $-30°$ to $+60°$ C., preferably at $0°-30°$ C.

Another method for introducing the amide group $NHR_3$ as $R_1$ involves reacting a 1-carboxylic acid of Formula I ($R_2=H$) wherein free hydroxy groups are optionally blocked intermediarily, with compounds of Formula IV $$O=C=N-R_3 \qquad IV$$

wherein $R_3$ is as defined above.

The reaction of the compound of Formula I ($R_1=OH$) with an isocyanate of Formula IV takes place, optionally, with the addition of a tertiary amine, such as, for example, triethylamine or pyridine. The reaction can be accomplished without a solvent or in an inert solvent, preferably acetonitrile, tetrahydrofuran, acetone, dimethylacetamide, methylene chloride, diethyl ether, toluene, etc., at temperatures of $-80°$ to $100°$ C., preferably at $0°-30°$ C.

If the starting compound contains OH-groups in the prostane residue, these OH-groups will also react. If, in the final analysis, end products are desired containing free hydroxy groups in the prostane moiety, then starting compounds are suitably employed wherein the OH groups are intermediarily blocked preferably by readily cleavable ether or acyl residues.

The carbacyclin derivatives of Formula I wherein $R_1$ is hydroxy ($R_2=H$) can be converted into salts with suitable amounts of the corresponding inorganic bases under conventional neutralizing conditions. For example, the solid inorganic salt is obtained when the corresponding acids are dissolved in water containing a stoichiometric quantity of the base, followed by evaporation of the water or addition of a water-miscible solvent, e.g., alcohol or acetone.

Amine salts are also prepared as usual. For this purpose, the carbacyclin acid can be dissolved, for example, in a suitable solvent such as ethanol, acetone, diethyl ether, or benzene, and at least a stoichiometric amount of the amine is added to this solution. During this step, the salt is ordinarily obtained in the solid phase or is isolated as usual after evaporation of the solvent.

The functional modification of the free OH-groups is conducted according to methods known to persons skilled in the art. For example, in order to introduce ether blocking groups, the reaction is carried out, e.g., with dihydropyran in methylene chloride or chloroform with the use of an acidic condensation agent, e.g., p-toluenesulfonic acid. Dihydropyran is used in excess, preferably in four to ten times the amount required theoretically. The reaction is normally completed at $0°-30°$ C. after 15–30 minutes.

Acyl blocking groups are also conventionally introduced, e.g., by reacting a compound of Formula I with a carboxylic acid derivative, for example an acid chloride, acid anhydride, etc.

The liberation of a functionally modified OH-group to obtain the compounds of Formula I again takes place by methods known per se. For example, ether blocking groups can be split off in an aqueous solution of an anorganic acid, e.g., hydrochloric acid. acetic acid, propionic acid, etc., or in an aqueous solution of an organic acid, e.g., hydrochloric acid. In order to improve solubility, a water-miscible, inert organic solvent is suitably added. Suitable organic solvents include, for example, alcohols, such as methanol and ethanol, and ethers, such as dimethoxyethane, dioxane, and tetrahydrofuran. Tetrahydrofuran is preferably employed. The splitting-off step is conducted preferably at temperatures of $20°$ to $80°$ C.

The silyl ether blocking groups are split off, for example, with tetrabutylammonium fluoride. Examples of suitable solvents include tetrahydrofuran, diethyl ether, dioxane, methylene chloride, etc. The splitting-off step is preferably conducted at temperatures of $0°$ to $80°$ C.

The acyl groups are saponified, for example, with alkali or alkaline earth metal carbonates or hydroxides in an alcohol or in the aqueous solution of an alcohol. Suitable alcohols are aliphatic alcohols, e.g., methanol, ethanol, butanol, etc., preferably methanol. Alkali metal carbonates and hydroxides that can be mentioned include potassium and sodium salts, but the potassium salts are preferred. Suitable alkaline earth metal carbonates and hydroxides include, for example calcium carbonate, calcium hydroxide, and barium carbonate. The reaction takes place at $-10°$ to $70°$ C., preferably at $25°$ C.

The starting materials of Formula II can be prepared, for example, by conventionally reacting an aldehyde of Formula V (DOS 2,845,770)

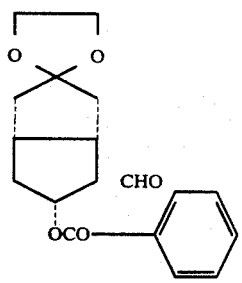

with a phosphonate of Formula VI

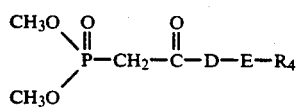

wherein D, E, and $R_4$ are as defined above, in the presence of a deprotonating agent, e.g., sodium hydride or potassium tert-butylate, to obtain a ketone of Formula VII (X=H) or additionally, in the presence of a brominating agent, for example N-bromosuccinimide, to a ketone of Formula VII (X=Br):

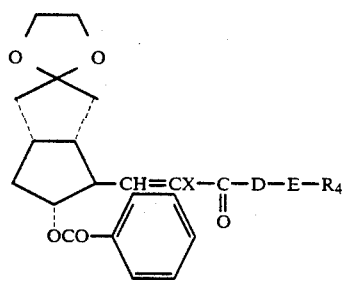

After conventional reduction of the keto group with zinc borohydride or sodium borohydride or reaction with alkyl magnesium bromide or alkyl lithium and subsequent separation of epimers, the compounds of Formula VIII are obtained:

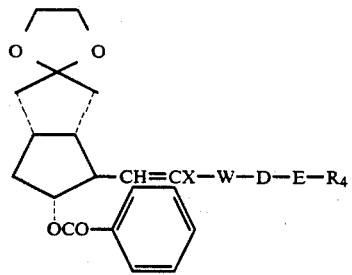

By saponification of the ester group, for example with potassium carbonate in methanol, as well as, optionally, hydrogenation of the double bond or, optionally, etherification with dihydropyran and subsequent splitting off of hydrogen bromide with, for example, potassium tert-butylate in dimethyl sulfoxide, ketal splitting with aqueous acetic acid, as well as, optionally, functional modification of the free hydroxy groups, for example by etherification with dihydropyran, the ketones of Formula IX are obtained:

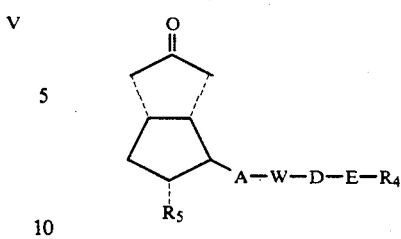

After a conventional olefin-forming reaction with phosphonofluoroacetic acid triethyl ester or phosphonofluoroacetic acid trimethyl ester, and subsequent reduction with lithium aluminum hydride, the compounds of Formula II isomeric in the double bond are obtained. These can optionally be separated.

The phosphonates of Formula VI can be produced in a manner known per se by reacting the anion of the dimethyl ester of methylphosphonic acid with an ester of Formula X

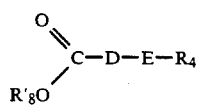

wherein
D, E, $R_4$ are as defined above and $R'_8$ is an alkyl group of 1-5 carbon atoms.

This ester can be conventionally obtained, if desired, from the corresponding malonic acid ester by alkylation with a halogenide of Formula XI:

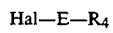

wherein Hal is chlorine or bromine, and subsequent decarbalkoxylation. The ester of Formula X is also conventionally obtainable, if desired, from the carboxylic acid of Formula XII

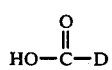

wherein D is as defined above, by alkylation with the halogenide of Formula XI and subsequent esterification.

As can be seen, all of the starting materials required for the preparation of the compounds of this invention are known or readily preparable using fully conventional techniques.

The compounds of this invention have blood-pressure-lowering and bronchodilatory effects. They are furthermore suitable for inhibiting thrombocyte aggregation. Consequently, the novel carbacyclin derivatives of Formula I represent valuable pharmacologically active agents. Moreover, with a similar spectrum of activity, they exhibit a higher specificity as compared with corresponding prostaglandins and, above all, a substantially longer efficacy. As compared with $PGI_2$, they are distinguished by higher stability.

The high tissue specificity of the novel prostaglandins is demonstrated in a study on smoothmuscle organs, such as, for example, on the guinea pig ileum or on the isolated rabbit trachea, where a substantially lower stimulation can be observed than in the administration of natural prostaglandins of the E-, A-, or F-type.

The novel carbacyclin analogs also exhibit the properties typical for prostacyclins, such as, for example, lowering of peripheral arterial and coronary vascular resistance, inhibition of thrombocyte aggregation and dissolution of platelet thrombi, myocardial cytoprotection and thus lowering of systemic blood pressure without simultaneously lowering stroke volume and coronary blood flow; treatment for stroke, prophylaxis and therapy of coronary heart disease, coronary thrombosis, cardiac infarction, peripheral arterial diseases, arteriosclerosis and thrombosis, prophylaxis and therapy of ischemic attacks of the CNS system, therapy for shock, inhibition of bronchoconstriction, inhibition of gastric acid secretion, cytoprotection for gastric and intestinal mucosa, cytoprotection in liver and pancreas, antiallergic properties, lowering of pulmonary vascular resistance and pulmonary blood pressure, promotion of kidney blood flow, utilization in place of heparin or as an adjuvant in dialysis of hemofiltration, preservation of blood plasma stores, especially blood platelet stores, inhibition of labor, treatment of gestational toxicosis, enhancement of cerebral blood flow, etc. In addition, the novel carbacyclin derivatives exhibit antiproliferative and antidiarrheogenic properties. The carbacyclins of this invention can also be utilized in combination, for example with β-blockers or diuretics.

The novel prostaglandin analogs of this invention are substantially more selective with regard to potency, as compared with known PG analogs, in causing prostaglandin-like biological responses, and have a substantially longer duration of biological activity. Accordingly, each of these novel prostaglandin analogs is surprisingly and unexpectedly more useful than one of the corresponding conventional prostaglandin-type compounds for at least one of the pharmacological purposes indicated above, because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

The usual dosage of the compounds is 1–1,500 µg/kg/day when administered to human patients. The unit dosage for the pharmaceutically acceptable carrier is usually 0.01–100 mg. Precise dosages in a given case can be readily determined using fully conventional methods, e.g., by differential potency tests vis a vis a known analogous agent such as $PGI_2$. In general, the administration of the compounds of this invention will be analagous to that of a related known agent, e.g., $PGI_2$.

Upon intravenous injection administered to nonanesthetized, hypertonic rats in doses of 5, 20, and 100 µg/kg/ body weight, the compounds of this invention exhibit a stronger blood-pressure-lowering effect and a more prolonged duration of efficacy than $PGE_2$ and $PGA_2$ without triggering diarrhea, as does $PGE_2$, or cardiac arrhythmias, as does $PGA_2$.

Upon intravenous injection administered to narcotized rabbits, the compounds of this invention show, as compared with $PGE_2$ and $PGA_2$, a stronger and also considerably prolonged blood-pressure-lowering effect without affecting other smooth-muscle organs or organ functions.

Sterile, injectable, aqueous or oily solutions are used for parenteral administration. Suitable for oral administration are, for example, tablets, dragees, or capsules. The invention accordingly also concerns medicinal agents based on the compounds of Formula I and conventional auxiliary agents and excipients. Thus, the active agents of this invention can serve, in conjunction with the excipients known and customary in galenic pharmacy, for example for the preparation of blood-pressure-lowering agents or agents corresponding to the many other uses of this invention.

The pharmacologically active compounds of this invention can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methyl-cellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5Z)-(16RS)-5-Fluoro-16-methyl-3-oxa-18,18,19,19-tetradehydro-6a-carbaprostaglandin $I_2$ 60.7 mg of 55% sodium hydride suspension in mineral oil is added to a solution of 310 mg of 2-[(Z)-(1S,5S,6R,7R)-7-(tetrahydropyran-2-yloxy)-6-[(E)-(3S,4RS)-4-methyl-3-(tetrahydropyran-2-yloxy)oct-1-en-6-ynyl]-bicyclo[3.3.0]octan-3-ylidene]-2-fluoroethan-1-ol in 10 ml of tetrahydrofuran; the reaction mixture is stirred for one hour under argon. After cooling to 0° C., a solution of 96.6 mg of bromoacetic acid in 3 ml of tetrahydrofuran is added dropwise to the mixture within one hour, and the mixture is then agitated at 20° C. for 26 hours, diluted with 150 ml of ether, and shaken four times with respectively 50 ml of 4% sodium hydroxide solution. This extract is adjusted to pH 3 with 10% sulfuric acid at 0° C. and extracted four times with respectively 50 ml of dichloromethane. The organic extract is shaken with 20 ml of brine, dried over magnesium sulfate, and evaporated under vacuum, obtaining 305 mg of (5Z)-(16RS)-5-fluoro-16-methyl-3-oxa-18,18,19,19-tetradehydro-6a-carbaprostaglandin I$_2$ 11,15-bis(tetrahydropyranyl ether); in order to split off the blocking groups, this product is stirred for 18 hours with 20 ml of acetic acid/water/tetrahydrofuran (65/35/10), then evaporated with the addition of toluene, the residue is chromatographed on silica gel with ethyl acetate/0.1–1% acetic acid, and 102 mg of the title compound is thus obtained as a colorless oil.

IR: 3600, 3400 (broad), 2955, 2920, 1731, 1601, 1108, 970 cm$^{-1}$.

The starting material for the above title compound is prepared as follows:

1(a)
2-[(Z)-(1S,5S,6R,7R)-7-(Tetrahydropyran-2-yloxy)-6-[(E)-(3S,4RS)-4-methyl-3-(tetrahydropyran-2-yloxy)oct-1-en-6-ynyl]bicyclo[3.3.0]octan-3-ylidene]-2-fluoroethan-1-ol A suspension is prepared from 128.4 mg of sodium hydride (55% strength mineral oil suspension) in 4 ml of dimethoxyethane; under argon, a solution of 791.5 mg of phosphonofluoroacetic acid triethyl ester in 2 ml of dimethoxyethane is added dropwise at 0° C. to the suspension, and the latter is agitated for 1.5 hours at 20° C. Then a solution of 775 mg of (1R,5S,6R,7R)-7-(tetrahydropyran-2-yloxy)-6-[(E)-3S,4RS)-4-methyl-3-(tetrahydropyran-2-yloxy)oct-1-en-6-ynyl]bicyclo[3.3.0]octan-3-one in 2 ml of dimethoxyethane is added dropwise thereto, and the mixture is stirred for 22 hours, then combined with 8 ml of water, and extracted three times with respectively 50 ml of ether. The extract is dried over magnesium sulfate and evaporated under vacuum, yielding 1.30 g of an oily product which, for purification, is chromatographed on silica gel with hexane/ether (1+1), obtaining in this way 500 mg of an oily ester which is dissolved for reducing purposes in 20 ml of ether and agitated at 0° C. for one hour with 180 mg of lithium aluminum hydride. The procut is combined with 0.75 ml of water, agitated for 2 hours at 20° C., filtered, and evaporated under vacuum. The residue is purified by chromatography on silica gel with hexane/10–90% ether. Elution yields first of all, as the less polar component, 195 mg of 2-[(E)-(1S,5S,6R,7R)-7-(tetrahydropyran-2-yloxy)-6-[(E)-(3S,4RS)-4-methyl-3-(tetrahydropyran-2-yloxy)oct-1-en-6-ynyl]bicyclo[3.3.0]octan-3-ylidene]-2-fluoroethan-1-ol and, as the more polar component., 198 mg of the title compound, both in the form of an oil.

IR: 3600, 3425, 2940, 1161, 970 cm$^{-1}$.

EXAMPLE 2

(5E)-(16RS)-5-Fluoro-16-methyl-3-oxa-18,18,19,19-tetradehydro-6a-carbaprostaglandin I$_2$ Analogously to Example 1, 180 mg of 2-[(E)-(1S,5S,-6R,7R)-7-(tetrahydropyran-2-yloxy)-6-[(E)-(3S,4RS)-4-methyl-3-(tetrahydropyran-2-yloxy)oct-1-en-6-ynyl]bicyclo[3.3.0]octan-3-ylidene]-2-fluoroethan-1-ol yields 45 mg of the title compound as a colorless oil.

IR: 3600, 3400 (broad), 2958, 2922, 1732, 1600, 1110, 974 cm$^{-1}$.

EXAMPLE 3

(5Z)-(16RS)-16,20-Dimethyl-5-fluoro-3-oxa-18,18,19,19-tetradehydro-6a-carbaprostaglandin I$_2$ In analogy to Example 1, 400 mg of 2-[(Z)(1S,5S,6R,7R)-7-(tetrahydropyran-2-yloxy)-6-[(E)-(3S,4RS)-4-methyl-3-(tetrahydropyran-2-yloxy)non-1-en-6-ynyl]bicyclo[3.3.0]octan-3-ylidene]-2-fluoroethan-1-ol yields 125 mg of the title compound as a colorless oil.

IR: 3600, 3405 (broad), 2954, 2920, 1730, 1601, 1115, 970 cm$^{-1}$.

The starting material for the above title compound is produced as follows:

3(a)
2-[(Z)-(1S,5S,6R,7R)-7-(Tetrahydropyran-2-yloxy)-6-[(E)-(3S,4RS)-4-methyl-3-(tetrahydropyran-2-yloxy)-non-1-en-6-ynyl]bicyclo[3.3.0]octan-3-ylidene]-2-fluoroethan-1-ol Analogously to Example 1(a), 1 g of (1R,5S,6R,7R)-7-(tetrahydropyran-2-yloxy)-6-[(E)-(3S,4RS)-4-methyl-3-(tetrahydropyran-2-yloxy)non-1-en-6-ynyl]bicyclo[3.3.0]octan-3-one yields, after chromatographic separation of isomers, as the less polar compound 235 mg of 2-[(E)-(1S,5S,6R,7R)-7-(tetrahydropyran-2-yloxy)-6-[(E)-(3S,4RS)-4-methyl-3-(tetrahydropyran-2-yloxy)non-1-en-6-ynyl]bicyclo[3.3.0]octan-3-ylidene]-2-fluoroethan-1-ol and 245 mg of the title compound as a colorless oil.

IR: 3600, 3422, 2945, 1165, 972 cm$^{-1}$.

EXAMPLE 4

(5Z)-5-Fluoro-20-methyl-3-oxa-18,18,19,19-tetradehydro-16,16-trimethylene-6a-carbaprostaglandin I$_2$ Analogously to Example 1, 200 mg of 2-[(Z)-(1S,5S,6R,7R)-7-(tetrahydropyran-2-yloxy)-6-[(E)-(3R)-3-(tetrahydropyran-2-yloxy)-4,4-trimethylene-non-1-en-6-ynyl]bicyclo[3.3.0]octan-3-ylidene]-2-fluoroethan-1-ol produces 58 mg of the title compound as a colorless oil.

IR: 3600, 3405 (broad), 2952, 2915, 1734, 1601, 1110, 970 cm$^{-1}$.

The starting material for the above title compound is prepared as set out below:

4(a)
2-[(Z)-(1S,5S,6R,7R)-7-(Tetrahydropyran-2-yloxy)-6-[(E)-(3R)-3-(tetrahydropyran-2-yloxy)-4,4-trimethylene-non-1-en-6-ynyl]bicyclo[3.3.0]octan-3-ylidene]-2-fluoroethan-1-ol Analogously to Example 1(a), 1 g of (1R,5S,6R,7R)-7-(tetrahydropyran-2-yloxy)-6-[(E)-(3R)-3-(tetrahydropyran-2-yloxy)-4,4-trimethylene-non-1-en-6-ynyl]bicyclo[3.3.0]octan-3-one yields, after chromatographic separation of isomers, as the less polar compound 220 mg of 2-[(E)-(1S,5S,6R,7R)-7-(tetrahydropyran-2-yloxy)-6-[(E)-(3R)-3-(tetrahydropyran-2-yloxy)-4,4-trimethylene-non-1-en-6-ynyl]bicyclo[3.3.0]octan-3-ylidene]-2-fluoroethan-1-ol and 240 mg of the title compound in the form of a colorless oil.

IR: 3600, 3410, 2945, 1160, 972 cm$^{-1}$.

EXAMPLE 5

(5Z)-16,16-Dimethyl-5-fluoro-3-oxa-18,18,19,19-tetradehydro-6a-carbaprostaglandin $I_2$ In analogy to Example 1, 420 mg of 2-[(Z)-(1S,5S,6R,7R)-7-(tetrahydropyran-2-yloxy)-6-[(E)-(3R)-4,4-dimethyl-3-(tetrahydropyran-2-yloxy)oct-1-en-6-ynyl]-bicyclo[3.3.0]octan-3-ylidene]-2-fluoroethan-1-ol yields 140 mg of the title compound as a colorless oil.

IR: 3600, 3400 (broad), 2958, 2921, 1732, 1601, 1110, 976 cm$^{-1}$.

The starting material for the above title compound is produced as follows:

5(a)

2-[(Z)-(1S,5S,6R,7R)-7-(Tetrahydropyran-2-yloxy)-6-[(E)-(3R)-4,4-dimethyl-3-(tetrahydropyran-2-yloxy)oct-1-en-6-ynyl]-bicyclo[3.3.0]octan-3-ylidene]-2-fluoroethan-1-ol Analogously to Example 1(a), 800 mg of (1R,5S,6R,7R)-7-(tetrahydropyran-2-yloxy)-6-[(E)-(3R)-4,4-dimethyl-3-(tetrahydropyran-2-yloxy)oct-1-en-6-ynyl]bicyclo[3.3.0]octan-3-one yields, after separation of isomers by chromatography, as the less polar compound 178 mg of 2-[(E)-(1S,5S,6R,7R)-7-(tetrahydropyran-2-yloxy)-6-[(E)-(3R)-4,4-dimethyl-3-(tetrahydropyran-2-yloxy)oct-1-en-6-ynyl]bicyclo[3.3.0]octan-3-ylidene]-2-fluoroethan-1-ol and 188 mg of the title compound as a colorless oil.

IR: 3405, 2950, 1162, 976 cm$^{-1}$.

EXAMPLE 6

(5Z)-5-Fluoro-3-oxa-16,16,20-trimethyl-18,18,19,19-tetradehydro-6a-carbaprostaglandin $I_2$ Analogously to Example 1, 400 mg of 2-[(Z)-(1S,5S,6R,7R)-7-(tetrahydropyran-2-yloxy)-6-[(E)-(3R)-4,4-dimethyl-3-(tetrahydropyran-2-yloxy)non-1-en-6-ynyl]bicyclo[3.3.0]octan-3-ylidene]-2-fluoroethan-1-ol yields 128 mg of the title compound as a colorless oil.

IR: 3600, 3405 (broad), 2960, 2922, 1735, 1601, 1116, 976 cm$^{-1}$.

The starting material for the above title compound is produced as set forth below:

6(a)

2-[(Z)-(1S,5S,6R,7R)-7-(Tetrahydropyran-2-yloxy)-6-[(E)-(3R)-4,4-dimethyl-3-(tetrahydropyran-2-yloxy)-non-1-n-6-ynyl]bicyclo[3.3.0]octan-3-ylidene]-2-fluoroethan-1-ol In analogy to Example 1(a), 2 g of (1R,5S,6R,7R)-7-(tetrahydropyran-2-yloxy)non-1-en-6-ynyl]bicyclo[3.3.0]octan-3-one yields, after isomer separation by chromatography, as the less polar compound 420 mg of 2-[(E)-(1S,5S,6R,7R)-7-(tetrahydropyran-2-yloxy)-6-[(E)-(3R)-4,4-dimethyl-3-(tetrahydropyran-2-yloxy)-non-1-en-6-ynyl]bicyclo[3.3.0]octan-3-ylidene]-2-fluoroethan-1-ol and 450 mg of the title compound as a colorless oil.

IR: 3600, 3410, 2952, 1160, 974 cm$^{-1}$.

EXAMPLE 7

(5Z)-(16RS)-16,19-Dimethyl-5-fluoro-18,19-didehydro-3-oxa-6a-carbaprostaglandin $I_2$ Analogously to Example 1, 150 mg of 2-[(Z)-(1S,5S,6R,7R)-7-(tetrahydropyran-2-yloxy)-6-[(E)-(3S,4RS)-4,7-dimethyl-3-(tetrahydropyran-2-yloxy)octa-1,6-dienyl]bicyclo[3.3.0]octan-3-ylidene]-2-fluoroethan-1-ol yields 48 mg of the title compound as a colorless oil.

IR: 3600, 3410 (broad), 2958, 2930, 1730, 1601, 1110, 976 cm$^{-1}$.

The starting material for the above title compound is produced as follows:

7(a)

2-[(Z)-(1S,5S,6R,7R)-7-(Tetrahydropyran-2-yloxy)-6-[(E)-(3R,4RS)-4,7-dimethyl-3-(tetrahydropyran-2-yloxy)octa-1,6-dienyl]bicyclo[3.3.0]octan-3-ylidene]-2-fluoroethan-1-ol In analogy to Example 1(a), 1 g of (1R,5S,6R,7R)-7-(tetrahydropyran-2-yloxy)-6-[(E)-(3R,4RS)-4,7-dimethyl-3-(tetrahydropyran-2-yloxy)octa-1,6-dienyl]bicyclo[3.3.0]octan-3-one produces, after chromatographic separation, as the less polar compound 240 mg of 2-[(E)-(1S,5S,6R,-7R)-7-(tetrahydropyran-2-yloxy)-6-[(E)-3S,4RS)-4,7-dimethyl-3-(tetrahydropyran-2-yloxy)octa-1,6-dienyl]bicyclo [3.3.0]octan-3-ylidene]-2-fluoroethan-1-ol and 250 mg of title compound as colorless oil.

IR: 3600, 3408, 2948, 1161, 970 cm$^{-1}$.

EXAMPLE 8

(5Z)-(16RS)-13,14-Didehydro-5-fluoro-16-methyl-3-oxa-18,18,19,19-tetradehydro-6a-carbaprostaglandin $I_2$ A solution of 300 mg of 2-[(Z)-(1S,5S,6R,7R)-7-(tetrahydropyran-2-yloxy)-6-[(3S,4RS)-4-methyl-3-(tetrahydropyran-2-yloxy)octa-1,6-diynyl]bicyclo[3.3.0]octan-3-ylidene]-2-fluoroethan-1-ol in 10 ml of tetrahydropyran is combined with 58.5 mg of sodium hydride (55% strength suspension in mineral oil). The mixture is agitated for one hour and, at 0° C. during the course of one hour, a solution of 94 mg of bromoacetic acid in 3 ml of tetrahydrofuran is added dropwise to the mixture; the latter is then stirred for 24 hours at 20° C., diluted with 150 ml of ether, and extracted four times with respectively 50 ml of 4% sodium hydroxide solution. This extract is adjusted at 0° C. to pH 3 with 10% sulfuric acid and extracted four times with respectively 50 ml of dichloromethane. .The combined dichloromethane extracts are shaken with 20 ml of brine, dried over magnesium sulfate, and evaporated under vacuum. The crude product is stirred for 18 hours with 20 ml of acetic acid/water/tetrahydrofuran (65/35/10), evaporated while adding toluene, and chromatographed on silica gel. With ethyl acetate/0.3% acetic acid, 110 mg of the title compound is eluted as a colorless oil.

IR: 3600, 3420 (broad), 2942, 2918, 1730, 1115 cm$^{-1}$.

The starting material for the above title compound is prepared as set out below:

8(a)

(1R,5S,6S,7R)-3,3-Ethylenedioxy-7-benzoyloxy-6-[(4RS)-2-bromo-4-methyl-3-oxooct-1-en-6-ynyl]bicyclo[3.3.0]octane At 0° C., a solution of 10.5 g of 3-methyl-2-oxohept-5-ynephosphonic acid dimethyl ester in 70 ml of dimethoxyethane is added dropwise to a suspension of 1.81 g of sodium hydride in 180 ml of dimethoxyethane; the mixture is stirred for one hour at 0° C. and then 7.4 g of finely pulverized N-bromosuccinimide is added thereto. The mixture is agitated for 30 minutes at 0° C., combined with a solution of 11.4 g of (1R,5S,6R,7R)-3,3-ethylenedioxy-7-benzoyloxy-6-formylbicyclo[3.3.0]octane in 90 ml of dimethoxyethane, and agitated for 2 hours at 0° C. The reaction mixture is poured on saturated ammonium chloride solution and extracted with ether. The organic extract is washed neutral with water, dried over magnesium sulfate, and evaporated under vacuum. Chromatography of the residue on silica gel yields, with hexane/ether (3+2), 8.2 g of the unsaturated ketone as a colorless oil.

IR: 2930, 2880, 1712, 1688, 1602, 1595, 1450, 1275, 945 cm$^{-1}$.

8(b)
(1R,5S,6S,7R)-3,3-Ethylenedioxy-7-(tetrahydropyran-2-yloxy)-6-[(3S,4RS)-2-bromo-4-methyl-3-(tetrahydropyran-2-yloxy)oct-1-en-6-ynyl]bicyclo[3.3.0]Octane At −40° C., 2.5 g of sodium borohydride is added in incremental portions to a solution of 5.9 g of the ketone prepared according to Example 8(a) in 140 ml of methanol, and the mixture is stirred for 30 minutes at −40° C. The mixture is then diluted with ether, washed neutral with water, dried over magnesium sulfate, and evaporated under vacuum. The crude product (mixture of 15-epimers) is dissolved in 200 ml of methanol, 2.5 g of potassium carbonate is added, and the mixture is agitated for 17 hours at 23° C. under argon. Subsequently the mixture is concentrated under vacuum, diluted with ether, and washed neutral with brine, then dried over magnesium sulfate and evaporated under vacuum. Column chromatography on silica gel with ether/methylene chloride yields first of all 1.6 g of the 15β-configured alcohol, and also, as the more polar component, 2.1 g of the title compound (PG nomenclature 15α-hydroxy) as colorless oils. A solution of 1.6 g of the α-alcohol, 16 mg of p-toluenesulfonic acid, and 1.5 g of dihydropyran in 50 ml of methylene chloride is agitated for 35 minutes at 0° C. Then the mixture is diluted with ether, shaken with dilute sodium carbonate solution, washed neutral with water, dried over magnesium sulfate, and evaporated under vacuum. Chromatography of the residue on silica gel yields, with hexane/ether (7+3), 2.17 g of the title compound as a colorless oil.

IR: 2940, 2870, 1450, 1120, 1018, 965, 948 cm$^{-1}$.

8(c)
(1R,5S,6S,7R)-7-(Tetrahydropyran-2-yloxy)-6-[(3S,4RS)-4-methyl-3-(tetrahydropyran-2-yloxy)octa-1,6-diynyl]bicyclo[3.3.0]octan-3-one A solution of 2.30 g of the compound obtained according to Example 8(b) in 23 ml of dimethyl sulfoxide and 10 ml of tetrahydrofuran is combined with 667 mg of potassium tert-butylate, and then stirred for 2 hours at 20° C. The mixture is diluted with 100 ml of water and extracted three times with respectively 100 ml of ether/hexane (8+2); the extract is washed with respectively 30 ml of water and brine, dried over magnesium sulfate, and evaporated under vacuum. The residue is stirred for 22 hours with 75 ml of acetic acid/water/tetrahydrofuran (65/35/10), evaporated under vacuum, and the residue is purified by chromatography on silica gel. With ether, 1.05 g of an oily compound is eluted which is reacted in 40 ml of dichloromethane with 0.91 g of dihydropyran and 10 mg of p-toluenesulfonic acid at 0° C. After 30 minutes, the mixture is diluted with ether, shaken with sodium bicarbonate solution and brine, dried over magnesium sulfate, and evaporated under vacuum. After chromatography on silica gel with hexane/ether (1+1), 1.53 g of the title compound is obtained as a colorless oil.

IR 2942, 2876, 2210, 1737, 1018, 970, 905, 868 cm$^{-1}$.

8(d)
2-[(Z)-(1S,5S,6S,7R)-7-(Tetrahydropyran-2-yloxy)-6-[(3S,4RS)-4-methyl-3-(tetrahydropyran-2-yloxy)octa-1,6-diynyl]bicyclo[3.3.0]-octan-3-ylidene]-2-fluoroethan-1-ol A suspension of 130 mg of sodium hydride (55% strength) in 6 ml of dimethoxyethane is combined with 800 mg of phosphonofluoroacetic acid triethyl ester. The mixture is stirred for one hour and then a solution of 800 mg of the ketone prepared according to Example 8(c) in 3 ml of dimethoxyethane is added dropwise thereto and the mixture stirred overnight at 20° C. After combining with 10 ml of water, the mixture is extracted three times with respectively 50 ml of ether; the extract is dried over magnesium sulfate and evaporated under vacuum. The oily residue is dissolved in 30 ml of anhydrous ether, combined in incremental portions at 0° C. with 250 mg of lithium aluminum hydride, agitated for one hour, and mixed dropwise with 1 ml of water, then with 100 ml of ether. The mixture is agitated for another hour at 20° C., filtered, and evaporated under vacuum. The residue is purified by chromatography on silica gel with hexane/20–80% ether. First of all, as the less polar compound, 200 mg of 2-[(E)-(1S,5S,6S,7R)-7-(tetrahydropyran-2-yloxy)-6-[(3S,4RS)-4-methyl-3-(tetrahydropyran-2-yloxy)-octa-1,6-diynyl]bicyclo[3.3.0]octan-3-ylidene]-2-fluoroethan-1-ol is eluted, and as the more polar compound, 210 mg of the title compound as a colorless oil.

IR: 3600, 3440, 2941, 2215, 1132, 1018, 971, 905, 865 cm$^{-1}$.

EXAMPLE 9

(5Z)-(16RS)-13,14-Didehydro-16,20-dimethyl-5-fluoro-3-oxa-18,18,19,19-tetradehydro-6-carbaprostaglandin I$_2$ Analogously to Example 8, 200 mg of 2-[(Z)-(1S,5S,6S,7R)-7-(tetrahydropyran-2-yloxy)-6-[(3S,4RS)-4-methyl-3-(tetrahydropyran-2-yloxy)nona-1,6-diynyl]-bicyclo[3.3.0]octan-3-ylidene]-2-fluoroethan-1-ol yields 80 mg of the title compound as a colorless oil.

IR: 3600, 3418 (broad), 2951, 2922, 1730, 1118 cm$^{-1}$.

The starting material for the above title compound is prepared as follows:

9(a)
(1R,5S,6S,7R)-3,3-Ethylenedioxy-7-benzoyloxy-6-[(4RS)-2-bromo-4-methyl-3-oxonon-1-en-6-ynyl]bicyclo[3.3.0]octane Analogously to Example 8(a), 12 g of the aldehyde used therein yields, with 3-methyl-2-oxooct-5-yne-phosphonic acid dimethyl ester, 8.80 g of the title compound as a colorless oil.

IR: 2935, 2880, 1715, 1601, 1593, 1451, 1270, 948 cm$^{-1}$.

9(b)
(1R,5S,6S,7R)-3,3-Ethylenedioxy-7-(tetrahydropyran-2-yloxy)-6-[(3S,4RS)-2-bromo-4-methyl-3-(tetrahydropyran-2-yloxy)non-1-en-6-ynyl]bicyclo[3.3.0]octane Analogously to Example 8(b), 8.50 g of the unsaturated ketone obtained according to Example 9(a) yields 3.65 g of the title compound as a colorless oil.

IR: 2938, 2878, 1450, 968, 948 cm$^{-1}$.

9(c)

(1R,5S,6S,7R)-7-(Tetrahydropyran-2-yloxy)-6-[(3S,4RS)-4-methyl-3-(tetrahydropyran-2-yloxy)nona-1,6-diynyl]bicyclo[3.3.0]octan-3-one In analogy to Example 8(c), 3.50 g of the compound produced according to Example 9(b) yields 2.41 g of the title compound as a colorless oil.

IR: 2940, 2875, 2218, 1738, 1020, 970, 906, 870 cm$^{-1}$.

9(d)

2-[(Z)-(1S,5S,6S,7R)-7-(Tetrahydropyran-2-yloxy)-6-[(3S,4RS)-4-methyl-3-(tetrahydropyran-2-yloxy)nona-1,6-diynyl]bicyclo[3.3.0]octan-3-ylidene]-2-fluoroethan-1-ol Analogously to Example 8(d), 2 g of the ketone prepared by following Example 9(c) yields, after separating isomers by chromatography, 490 mg of less polar 2-[(E)-(1S,5S,6S,7R)-7-(tetrahydropyran-2-yloxy)-6-[(3S,4RS)-4-methyl-3-(tetrahydropyran-2-yloxy)nona-1,6-diynyl]bicyclo[3.3.0]octan-3-ylidene]-2-fluoroethan-1-ol and, as the more polar component, 505 mg of the title compound as a colorless oil.

IR: 3600, 3435, 2940, 2210, 1130, 1015, 970, 905, 868 cm$^{-1}$.

EXAMPLE 10

(5Z)-13,14-Didehydro-5-fluoro-20-methyl-3-oxa-18,18,19,19-tetradehydro-16,16-trimethylene-6a-carbaprostaglandin I$_2$ Analogously to Example 8, 200 mg of 2-[(Z)-(1S,5S,6S,7R)-7-(tetrahydropyran-2-yloxy)-6-[(3S)-3-tetrahydropyran-2-yloxy)-4,4-trimethylene-nona-1,6-diynyl]bicyclo[3.3.0]octan-3-ylidene]-2-fluoroethan-1-ol yields 90 mg of the title compound as a colorless oil.

IR: 3600, 3420 (broad), 2950, 2920, 1732, 1116 cm$^{-1}$.

The starting material for the above title compound is prepared as follows:

10(a)

(1R,5S,6S,7R)-3,3-Ethylenedioxy-7-benzoyloxy-6-(2-bromo-3-oxo-4,4-trimethylene-non-1-en-6-ynyl)bicyclo[3.3.0]octane Analogously to Example 8(a), using 2-oxa-3,3-trimethyleneoct-5-ynephosphonic acid dimethyl ester, 9.01 g of the title compound is obtained as a colorless oil from 10 g of the aldehyde employed in Example 8(a).

IR: 2938, 2880, 1712, 1690, 1600, 1592, 1451, 1273, 948 cm$^{-1}$.

10(b)

(1R,5S,6S,7R)-3,3-Ethylenedioxy-7-(tetrahydropyran-2-yloxy)-6-[(3S)-2-bromo-3-(tetrahydropyran-2-yloxy)-4,4-trimethylene-non-1-en-6-ynyl]bicyclo[3.3.0]octane In analogy to Example 8(b), 9 g of the compound produced according to Example 10(a) yields 3.40 g of the title compound as a colorless oil.

IR: 2940, 2880, 1451, 970, 948 cm$^{-1}$.

10(c)

(1R,5S,6S,7R)-7-(Tetrahydropyran-2-yloxy)-6-[(3S)-3-(tetrahydropyran-2-yloxy)-4,4-trimethylene-nona-1,6-diynyl]bicyclo[3.3.0]octan-3-one Analogously to Example 8(c), 3.31 g of the compound prepared according to Example 10(b) yields 2.05 g of the title compound as a colorless oil.

IR: 2945, 2878, 2210, 1736, 1015, 970, 906, 869 cm$^{-1}$.

10(d)

2-[(Z)-(1S,5S,6S,7R)-7-(Tetrahydropyran-2-yloxy)-6-[(3S)-3-(tetrahydropyran-2-yloxy)-4,4-trimethylene-nona-1,6-diynyl]bicyclo[3.3.0]octan-3-ylidene]-2-fluoroethan-1-ol In analogy to Example 8(d), 2 g of the ketone prepared according to Example 10(c) yields, after chromatographic separation, 430 mg of less polar 2-[(E)-(1S,5S,6S,7R)-7-(tetrahydropyran-2-yloxy)-6-[(3S)-3-(tetrahydropyran-2-yloxy)-4,4-trimethylene-nona-1,6-diynyl]bicyclo[3.3.0]octan-3-ylidene]-2-fluoroethan-1-ol and, as the more polar component, 505 mg of the title compound as a colorless oil.

IR: 3600, 3420, 2942, 2215, 1135, 1013, 970, 908, 870 cm$^{-1}$.

EXAMPLE 11

(5Z)-13,14-Didehydro-16,16-dimethyl-5-fluoro-3-oxa-18,18,19,19-tetradehydro-6a-carbaprostaglandin I$_2$ Analogously to Example 8, 180 mg of 2-[(Z)-(1S,5S,6S,7R)-7-(tetrahydropyran-2-yloxy)-6-[(3S)-4,4-dimethyl-3-(tetrahydropyran-2-yloxy)octa-1,6-diynyl]bicyclo[3.3.0]octan-3-ylidene]-2-fluoroethan-1-ol yields 85 mg of the title compound as a colorless oil.

IR: 3600, 3420 (broad), 2948, 2922, 1731, 1120 cm$^{-1}$.

The starting material for the above title compound is prepared as follows:

11(a)

(1R,5S,6S,7R)-3,3-Ethylenedioxy-7-benzoyloxy-6-(2-bromo-4,4-dimethyl-3-oxooct-1-en-6-ynyl)bicyclo[3.3.0]octane Analogously to Example 8(a), using 3,3-dimethyl-2-oxohept-5-ynephosphonic acid dimethyl ester and 10 g of the aldehyde used therein, 7.90 g of the title compound is produced as a colorless oil.

IR: 2935, 2875, 1710, 1685, 1601, 1594, 1450, 1270, 947 cm$^{-1}$.

11(b)

(1R,5S,6S,7R)-3,3-Ethylenedioxy-7-(tetrahydropyran-2-yloxy)-6-[(3S)-2-bromo-4,4-dimethyl-3-(tetrahydropyran-2-yloxy)oct-1-en-6-ynyl]bicyclo[3.3.0]octane Analogously to Example 8(b), 7.85 g of the unsaturated ketone obtained according to Example 11(a) yields 3.32 g of the title compound as a colorless oil.

IR: 2940, 2877, 1451, 970, 948 cm$^{-1}$.

(c)

(1R,5S,6S,7R)-7-(Tetrahydropyran-2-yloxy)-6-[(3S)-4,4-dimethyl-3-(tetrahydropyran-2-yloxy)octa-1,6-diynyl]bicyclo[3.3.0]octan-3-one In analogy to Example 8(c), 3.21 g of the compound prepared according to Example 11(b) yields 2.05 g of the title compound as a colorless oil.

IR: 2945, 2875, 2213, 1740, 1025, 970, 906, 871 cm$^{-1}$.

(d)

2-[(Z)-(1S,5S,6S,7R)-7-(Tetrahydropyran-2-yloxy)-6-[(3S)-4,4-dimethyl-3-(tetrahydropyran-2-yloxy)octa-1,6-diynyl]bicyclo[3.3.0]octan-3-ylidene]-2-fluoroethan-1-ol Analogously to Example 8(d), 2 g of the ketone produced according to Example 11(c) yields, after separation of isomers by chromatography, 480 mg of less polar 2-[(E)-(1S,5S,6S,7R)-7-(tetrahydropyran-2-yloxy)-6-

(3S)-4,4-dimethyl-3-(tetrahydropyran-2-yloxy)octa-1,6-diynyl]bicyclo[3.3.0]octan-3-ylidene]-2-fluoroethan-1-ol and, as the more polar component, 525 mg of the title compound as a colorless oil.

IR: 3600, 3430, 2940, 2212, 1135, 1021, 970, 908, 871 cm$^{-1}$.

EXAMPLE 12

(5Z)-13,14-Didehydro-5-fluoro-3-oxa-18,18,19,19-tetradehydro-16,16,20-trimethyl-6a-carbaprostaglandin $I_2$ Analogously to Example 8, 150 mg of 2-[(Z)-(1S,5S,6S,7R)-7-(tetrahydropyran-2-yloxy)-6-[(3S)-4,4-dimethyl-3-(tetrahydropyran-2-yloxy)nona-1,6-diynyl]bicyclo[3.3.0]octan-3-ylidene]-2-fluoroethan-1-ol produces 68 mg of the title compound as a colorless oil.

IR: 3600, 3415 (broad), 2951, 2925, 1731, 1128 cm$^{-1}$.

The starting compound for the above product is prepared as follows:

12(a)

(1R,5S,6S,7R)-3,3-Ethylenedioxy-7-benzoyl-oxy-6-(2-bromo-4,4-dimethyl-3-oxonon-1-en-6-ynyl)bicyclo[3.3.0]octane Analogously to Example 8(a), using 3,3-dimethyl-2-oxooct-5-ynephosphonic acid dimethyl ester and 12 g of the aldehyde utilized in Example 8(a), 8.10 g of the title compound is obtained as a colorless oil.

IR: 2938, 2882, 1711, 1685, 1600, 1593, 1450, 1273, 948 cm$^{-1}$.

12(b)

(1R,5S,6S,7R)-3,3-Ethylenedioxy-7-(tetrahydropyran-2-yloxy)-6-[(3S)-2-bromo-4,4-dimethyl-3-(tetrahydropyran-2-yloxy)non-1-en-6-ynyl]bicyclo[3.3.0]octane Analogously to Example 8(b), 8.00 g of the unsaturated ketone obtained according to Example 12(a) yields 3.51 g of the title compound as a colorless oil.

IR: 2941, 2875, 1450, 971, 948 cm$^{-1}$.

12(c)

(1R,5S,6S,7R)-7-(Tetrahydropyran-2-yloxy)-6-[(3S)-4,4-dimethyl-3-(tetrahydropyran-2-yloxy)nona-1,6-diynyl]bicyclo[3.3.0]octan-3-one In analogy to Example 8(c), 3.30 g of the compound prepared according to Example 12(b) produces 2.15 g of the title compound as a colorless oil.

IR: 2950, 2872, 2210, 1737, 1022, 970, 905, 870 cm$^{-1}$.

12(d)

2-[(Z)-(1S,5S,6S,7R)-7-(Tetrahydropyran-2-yloxy)-6-[(3S)-4,4-dimethyl-3-(tetrahydropyran-2-yloxy)nona-1,6-diynyl]bicyclo[3.3.0]octan-3-ylidene]-2-fluoroethan-1-ol Analogously to Example 8(d), 2 g of the ketone prepared according to Example 12(c) yields, after isomer separation by chromatography, 435 mg of less polar 2-[(E)-(1S,5S,6S,7R)-7-(tetrahydropyran-2-yloxy)-6-[(3S)-4,4-dimethyl-3-(tetrahydropyran-2-yloxy)nona-1,6-diynyl]bicyclo[3.3.0]octan-3-ylidene]-2-fluoroethan-1-ol and, as the more polar component, 570 mg of the title compound as a colorless oil.

IR: 3600, 3410, 2938, 2217, 1138, 1018, 970, 871 cm$^{1}$.

EXAMPLE 13

(5Z)-(16RS)-5-Fluoro-16-methyl-3-oxa-18,18,19,19-tetradehydro-6a-carbaprostaglandin $I_2$ Methyl Ester 100 mg of (5Z)-(16RS)-5-fluoro-16-methyl-3-oxa-18,18,19,19-tetradehydro-6a-carbaprostaglandin $I_2$ is dissolved in 20 ml of dichloromethane and, at 0° C., an ethereal diazomethane solution is added dropwise thereto until the mixture assumes a permanent yellow coloring. After 5 minutes, the mixture is evaporated under vacuum and the residue adsorbed on silica gel and eluted with hexane/ethyl acetate 20–70%, thus obtaining 82 mg of the title compound as a colorless oil.

IR: 3600, 3410, 2955, 1741, 976 cm$^{-1}$.

EXAMPLE 14

(5Z)-(16RS)-5-Fluoro-16-methyl-3-oxa-18,18,19,19-tetradehydro-6a-carbaprostaglandin $I_2$ Carboxamide A solution of 185 mg of (5Z)-(16RS)-5-fluoro-16-methyl-3-oxa-18,18,19,19-tetradehydro-6a-carbaprostaglandin $I_2$ (see Example 1) in 5 ml of dimethylformamide is combined at 0° C. with 60 mg of triethylamine and 80 mg of chloroformic acid isobutyl ester. After 30 minutes, dry gaseous ammonia is introduced for 15 minutes. The mixture is allowed to stand for 2 hours at 20° C., diluted with citrate buffer (pH 5), extracted several times with ethyl acetate, the extract is washed with sodium bicarbonate solution and brine, dried over magnesium sulfate, and evaporated under vacuum. Chromatography of the residue on silica gel with dichloromethane/1–5% isopropanol yields 135 mg of the title compound as a colorless oil.

IR: 3600, 3510, 3410, 2953, 1668, 976 cm$^{-1}$.

EXAMPLE 15

(5Z)-(16RS)-5-Fluoro-16-methyl-3-oxa-18,18,19,19-tetradehydro-6a-carbaprostaglandin $I_2$
(2,3-Dihydroxypropyl)amide A solution is prepared of 345 mg of (5Z)-(16RS)-5-fluoro-16-methyl-3-oxa-18,18,19,19-tetradehydro-6a-carbaprostaglandin $I_2$ 11,15-bis(tetrahydropyranyl ether) in 5 ml of acetone and combined at 0° C. with 74 mg of triethylamine and 100 mg of chloroformic acid isobutyl ester. After 20 minutes, a solution of 574 mg of 1-amino-2,3-dihydroxypropane in 10 ml of acetone and 10 ml of acetonitrile is added thereto and the mixture stirred for one hour at 20° C. The mixture is then concentrated under vacuum, diluted with 100 ml of dichloromethane, washed with brine, dried over magnesium sulfate, and evaporated under vacuum.

The residue is stirred for 18 hours at 20° C. with 10 ml of acetic acid/water/tetrahydrofuran (65/35/10), evaporated under vacuum, and the residue purified by column chromatography on silica gel. With dichloromethane/isopropanol (5–20%), 253 mg of the title compound is eluted as a colorless oil.

IR 3600, 3390, 2931, 1642, 976 cm$^{-1}$.

EXAMPLE 16

(5Z)-(16RS)-5-Fluoro-16-methyl-3-oxa-18,18,19,19-tetradehydro-6a-carbaprostaglandin $I_2$ Acetylamide At 20° C., a solution of 265 mg of (5Z)-(16RS)-5-fluoro-16-methyl-3-oxa-18,18,19,19-tetradehydro-6a-carbaprostaglandin $I_2$ 11,15-bis(tetrahydropyranyl ether) (see Example 1) in 8 ml of acetonitrile is combined with 65 mg of triethylamine, cooled to 0° C., and then a solution of 48 mg of acetyl isocyanate in 5 ml of acetonitrile is added dropwise thereto. After 2 hours at 20° C., the mixture is concentrated under vacuum, diluted with 100 ml of citrate buffer (pH 5), extracted with ether, the extract is washed in succession with sodium bicarbonate solution and brine, dried over magnesium sulfate, and evaporated under vacuum. In order to split off the blocking groups, the residue is stirred overnight with 10 ml of glacial acetic acid/water/tetrahydrofuran (65/35/10) and evaporated to dryness under vacuum. The residue is chromatographed on silica gel with dichloromethane/1% isopropanol, thus obtaining 105 mg of the title compound as a colorless oil.

IR: 3600, 3405, 1707, 972 cm$^{-1}$.

EXAMPLE 17

(5Z)-(16RS)-5-Fluoro-16-methyl-3-oxa-18,18,19,19-tetradehydro-6a-carbaprostaglandin I$_2$ (4-Phenyl)phenacyl Ester 15 mg of (5Z)-(16RS)-5-fluoro-16-methyl-3-oxa-18,18,19,19-tetradehydro-6a-carbaprostaglandin I$_2$ is dissolved in 3 ml of acetone and combined with 87 mg of ω-bromo-4-phenylacetophenone and 1 ml of triethylamine, and stirred overnight under argon at room temperature. The mixture is combined with 200 ml of ether, shaken twice with respectively 10 ml of water, dried over magnesium sulfate, and evaporated under vacuum. Purification is by preparative layer chromatography on silica gel plates developed with dichloromethane/10% isopropanol, thus obtaining 152 mg of the title compound as an oil.

IR: 3600, 2938, 1740, 1702, 1601, 974 cm$^{-1}$.

EXAMPLE 18

(5Z)-(16RS)-5-Fluoro-16-methyl-3-oxa-18,18,19,19-tetradehydro-6a-carbaprostaglandin I$_2$ Tris(hydroxymethyl)aminomethane Salt At 68° C., a solution of 60 mg of tris(hydroxymethyl)aminomethane in 0.2 ml of water is added to a solution of 208 mg of (5Z)-(16RS)-5-fluoro-16-methyl-3-oxa-18,18,19,19-tetradehydro-6a-carbaprostaglandin I$_2$ in 35 ml of acetonitrile. The mixture is allowed to cool down under stirring, decanted from the solvent after 16 hours, and the residue is dried under vacuum, thus isolating 192 mg of the title compound as a viscous oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A carbacyclin of the formula

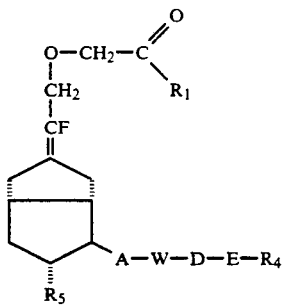

wherein
R$_1$ is OR$_2$,
wherein
R$_2$ is (a) hydrogen, (b) C$_{1-10}$ alkyl, (c) C$_{1-10}$ alkyl substituted by halogen; hydroxy; C$_{1-4}$ alkoxy; C$_{6-10}$ aryl; C$_{6-10}$ aryl substituted by 1-3 halogen atoms, a phenyl group 1-3 C$_{1-4}$ alkyl groups or a chloromethyl, fluoromethyl, trifluoromethyl, carboxy, hydroxy or C$_{1-4}$ alkoxy group; di-C$_{1-4}$-alkylamino; or tri-C$_{1-4}$-alkylammonium; (d) C$_{3-10}$ cycloalkyl, (e) C$_{3-10}$ cycloalkyl substituted by C$_{1-4}$ alkyl, (f) C$_{6-10}$ aryl, (g) C$_{6-10}$ aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group, or (h) an aromatic heterocycle of 5 or 6 ring atoms one of which is O, N or S, the remainder being carbon atoms,
or R$_1$ is NHR$_3$, where R$_3$ is R$_2$ or the acyl group of a C$_{1-15}$-hydrocarboncarboxylic or sulfonic acid;
A is —C≡C—;
W is —CHOR—, or

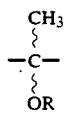

wherein the OR-group is in the α- or β-position;
R is H, tetrahydropyranyl, tetrahydrofuranyl, α-ethoxyethyl, trimethylsilyl, dimethyl-tert-butylsilyl, tribenzylsilyl or an acyl group of a C$_{1-15}$-hydrocarbon carboxylic or sulfonic acid; or
D is

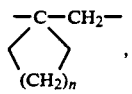

C$_{2-10}$-alkylene, which is optionally substituted by fluorine;
n is 1, 2, or 3;
E is —C≡C—, in each case in the 18-position (prostanoic acid nomenclature),
wherein
R$_5$ is OR;
R$_4$ is (a) a C$_{1-10}$ hydrocarbon aliphatic radical, (b) a C$_{1-10}$ hydrocarbon aliphatic radical substituted by C$_{6-10}$ aryl or by C$_{6-10}$ aryl substituted by 1-3 halogen atoms; a phenyl group 1-3 C$_{1-4}$ alkyl groups or a chloromethyl, fluoromethyl, trifluoromethyl, carboxy, hydroxy or C$_{1-4}$ alkoxy group; (c) C$_{3-10}$ cycloalkyl, (d) C$_{3-10}$ cycloalkyl substituted by C$_{1-4}$ alkyl, (e) $C_{6-10}$ aryl, (f) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; or (h) an aromatic heterocycle of 5 or 6 ring atoms one of which is O, N or S, the remainder being carbon atoms;

or when $R_1$ is OH, a physiologically compatible salt thereof with a base.

2. A compound of claim 1 wherein
$R_1$ is OH, O-$C_{1-4}$-alkyl; $NH_2$; or $NH(C_{1-4}$-alkyl).

3. A compound of claim 1 wherein $R_2$ is (d) or (e) as defined in claim 1.

4. A compound of claim 1 wherein $R_2$ is (h) as defined in claim 1.

5. A compound of claim 1 wherein
D is

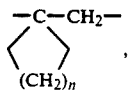

6. (5Z)-(16S)-13,14-Didehydro-5-fluoro-16-methyl-3-oxa-18,18,19,19-tetradehydro-6a-carbaprostaglandin $I_2$, a compound of claim 1.

7. (5Z)-(16RS)-13,14-Didehydro-16,20-dimethyl-5-fluoro-3-oxa-18,18,19,19-tetradehydro-6a-carbaprostaglandin $I_2$, a compound of claim 1.

8. (5Z)-13,14-Didehydro-5-fluoro-20-methyl-3-oxa-18,18,19,19-tetradehydro-16,16-trimethylene-6a-carbaprostaglandin $I_2$, a compound of claim 1.

9. (5Z)-13,14-Didehydro-16,16-dimethyl-5-fluoro-3-oxa-18,18,19,19-tetradehydro-6a-carbaprostaglandin $I_2$, a compound of claim 1.

10. (5Z)-13,14-Didehydro-5-fluoro-3-oxa-18,18,19,19-tetradehydro-16,16,20-trimethyl-6a-carbaprostaglandin $I_2$, a compound of claim 1.

11. A pharmaceutical composition comprising an amount of a compound of claim 1 effective to lower blood pressure and a pharmaceutically acceptable carrier.

12. A method of inhibiting thrombocyte aggregation patient in need of such treatment, comprising administering to the patient an amount of a compound of claim 1 effective for such treatment.

13. A compound of claim 1 wherein —A—W—D—E—$R_4$ is:

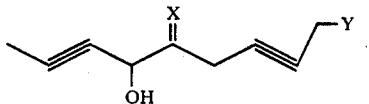

wherein:
Y is H or $CH_3$; and
X is H, $CH_3$; H, H; $CH_3$, $CH_3$; or —$CH_2$—$CH_2$—$CH_2$—.

* * * * *